(12) United States Patent
Muramatsu et al.

(10) Patent No.: US 11,076,106 B2
(45) Date of Patent: Jul. 27, 2021

(54) OBSERVATION SYSTEM AND LIGHT SOURCE CONTROL APPARATUS

(71) Applicant: Sony Corporation, Tokyo (JP)

(72) Inventors: Hirotaka Muramatsu, Kanagawa (JP); Takashi Yamaguchi, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 0 days.

(21) Appl. No.: 16/613,811

(22) PCT Filed: Feb. 16, 2018

(86) PCT No.: PCT/JP2018/005475
§ 371 (c)(1),
(2) Date: Nov. 15, 2019

(87) PCT Pub. No.: WO2018/216276
PCT Pub. Date: Nov. 29, 2018

(65) Prior Publication Data
US 2020/0154028 A1 May 14, 2020

(30) Foreign Application Priority Data
May 22, 2017 (JP) .............................. JP2017-100738

(51) Int. Cl.
H04N 5/235 (2006.01)
H04N 9/07 (2006.01)

(52) U.S. Cl.
CPC ............ *H04N 5/2354* (2013.01); *H04N 9/07* (2013.01)

(58) Field of Classification Search
CPC .... H04N 5/2256; H04N 5/235; H04N 5/2354; H04N 9/07
See application file for complete search history.

(56) References Cited

U.S. PATENT DOCUMENTS

2011/0063427 A1*  3/2011  Fengler ................ A61B 1/0638
                                              348/65
2011/0071352 A1*  3/2011  Ozawa ................. A61B 1/0638
                                              600/109
2016/0106299 A1*  4/2016  Kamee ............... A61B 1/00045
                                              348/67

FOREIGN PATENT DOCUMENTS

JP  2007-117583 A  5/2007
JP  2012-152460 A  8/2012
(Continued)

OTHER PUBLICATIONS

International Search Report and Written Opinion dated May 22, 2018 for PCT/JP2018/005475 filed on Feb. 16, 2018, 10 pages including English Translation of the International Search Report.

Primary Examiner — Ahmed A Berhan
(74) Attorney, Agent, or Firm — Xsensus LLP

(57) ABSTRACT

To provide an observation system and a light source control apparatus capable of more efficiently generating observation light to be used for special observation different from normal observation, and enabling the special observation to be more efficiently performed.
An observation system includes: a plurality of light sources that emits light of different wavelength bands that can be combined to generate white light; an optical system that irradiates an observation object with first light that includes light emitted from some of the plurality of light sources; an imaging device that captures an image of the observation object irradiated with the first light; and a light source control unit that controls the quantity of the first light on the basis of the luminance of a pixel corresponding to a predetermined wavelength band in the captured image.

11 Claims, 8 Drawing Sheets

(56) References Cited

FOREIGN PATENT DOCUMENTS

| | | |
|---|---|---|
| JP | 2013-176 A | 1/2013 |
| JP | 5308815 B2 | 10/2013 |
| JP | 2015-25965 A | 2/2015 |
| JP | 2016-41388 A | 3/2016 |

* cited by examiner

OBSERVATION SYSTEM AND LIGHT SOURCE CONTROL APPARATUS

CROSS-REFERENCE TO RELATED APPLICATIONS

The present application is based on PCT filing PCT/JP2018/005475, filed Feb. 16, 2018, which claims priority to JP 2017-100738, filed May 22, 2017, the entire contents of each are incorporated herein by reference.

TECHNICAL FIELD

The present disclosure relates to an observation system and a light source control apparatus.

BACKGROUND ART

In recent years, an observation system which includes a light source and an imaging device for observing a living body is widely used in the medical field and the like. Examples of the observation system include an endoscope and a microscope.

For example, in such an observation system, an observation object is irradiated with white light to capture an observation image similar to observation with the naked eye (also referred to as normal observation). In addition, a fluorescent substance that is likely to accumulate in a specific tissue is administered to the observation object to enable observation of the specific tissue emphasized with the fluorescence of the fluorescent substance (also referred to as special observation).

For example, Patent Document 1 below discloses a biological observation system that modulates the wavelength of light emitted from a white lamp light source to an observation object by using a rotary filter including multiple optical filters that only transmit respective specific wavelength bands different from each other. The biological observation system rotates the rotary filter in synchronization with imaging timing to obtain each of a red image, a green image, and a blue image corresponding to RGB signals.

CITATION LIST

Patent Document

Patent Document 1: Japanese Patent No. 5308815

SUMMARY OF THE INVENTION

Problems to be Solved by the Invention

However, the biological observation system disclosed in Patent Document 1 described above is low in energy efficiency in generating observation light. This is because the biological observation system uses a wavelength band partially taken out from wide-band white light. Furthermore, the rotary filter including various optical filters and the rotation control mechanism of the rotary filter are likely to be complicated in the biological observation system. Thus, the biological observation system tends to be large.

Therefore, the present disclosure proposes a new and improved observation system and a light source control apparatus capable of more efficiently generating observation light to be used for special observation different from normal observation, and enabling the special observation to be more efficiently performed.

Solutions to Problems

According to the present disclosure, there is provided an observation system including: a plurality of light sources that emits light of different wavelength bands that can be combined to generate white light; an optical system that irradiates an observation object with first light that includes light emitted from some of the plurality of light sources; an imaging device that captures an image of the observation object irradiated with the first light; and a light source control unit that controls the quantity of the first light on the basis of the luminance of a pixel corresponding to a predetermined wavelength band in the captured image.

Furthermore, according to the present disclosure, there is provided a light source control apparatus including: a light source control unit that controls the quantity of first light to be applied to an observation object on the basis of the luminance of a pixel corresponding to a predetermined wavelength band in a captured image of the observation object, in which the first light includes light emitted from some of a plurality of light sources that emits light of different wavelength bands that can be combined to generate white light.

According to the present disclosure, it is possible to generate light of a specific wavelength band to be used for special observation, by using light emitted from some of a plurality of light sources that emits light that can be combined to generate white light.

Furthermore, it is possible to obtain a captured image with less variation in luminance in special observation by controlling the quantity of light of a specific wavelength band on the basis of the luminance of a pixel of the captured image at the time of special observation.

Effects of the Invention

As described above, according to the present disclosure, it is possible to more efficiently generate observation light to be used for special observation different from normal observation, and to perform the special observation more efficiently.

Note that the above-described effect is not necessarily restrictive, and any of the effects set forth in the present specification or another effect that can be derived from the present specification may be achieved together with or instead of the above-described effect.

MODE FOR CARRYING OUT THE INVENTION

A preferred embodiment of the present disclosure will be described in detail below with reference to the accompanying drawings. Note that in the present specification and the drawings, the same reference signs are assigned to constituent elements having substantially the same functional configurations, and redundant description will be thus omitted.

Note that descriptions will be provided in the following order.

1. Configuration Example of Observation System
2. Operation Example of Observation System
3. Control Patterns of Observation Light
3.1. First Control Pattern
3.2. Second Control Pattern
3.3. Third Control Pattern
3.4. Fourth Control Pattern
4. Specific Example of Observation System
5. Supplementary Notes <1. Configuration Example of Observation System>

Figure 1:
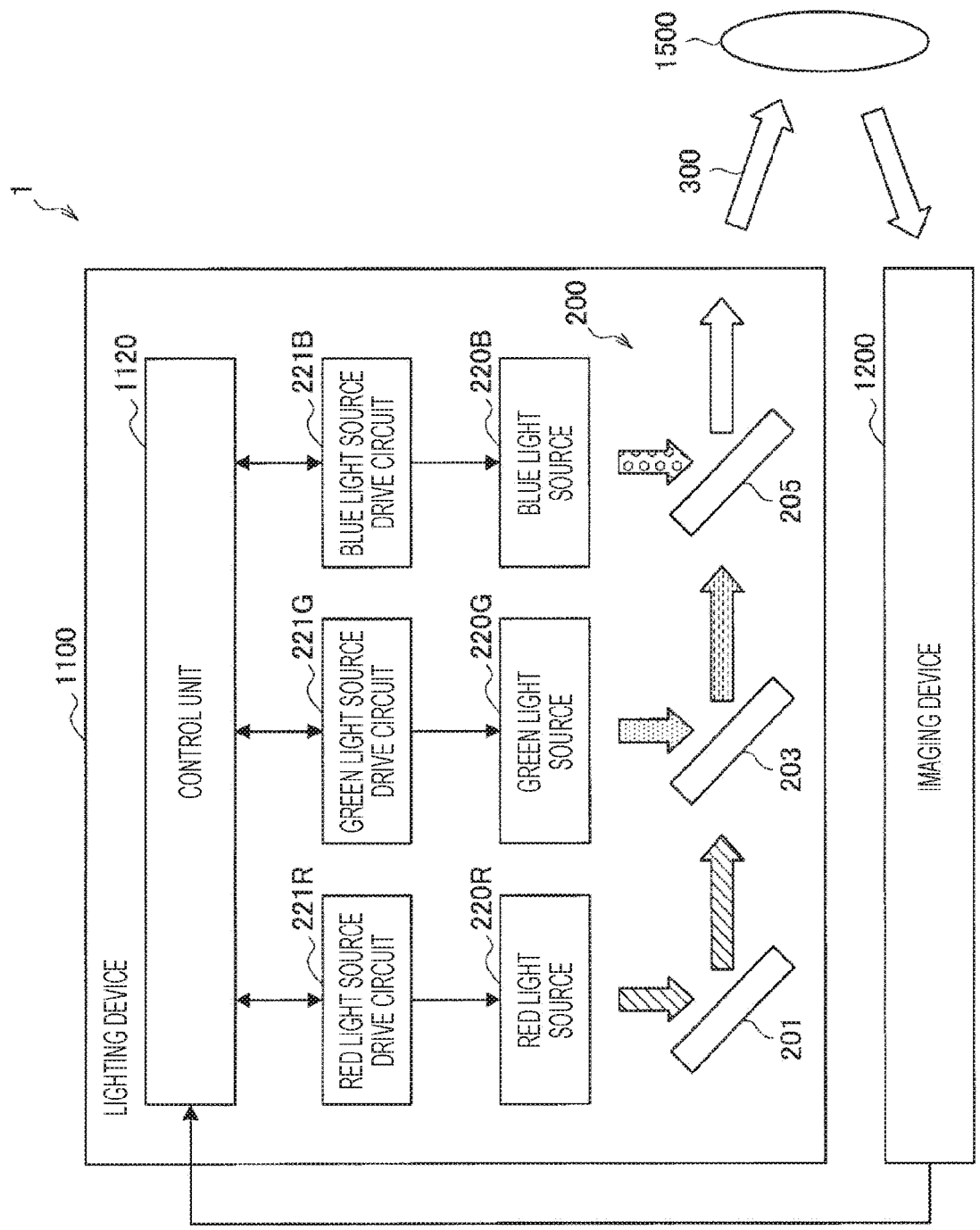
FIG. 1 is an explanatory diagram showing a configuration example of an observation system according to an embodiment of the present disclosure.

First, a configuration example of an observation system according to an embodiment of the present disclosure will be described with reference to FIG. 1. FIG. 1 is an explanatory diagram showing a configuration example of an observation system 1 according to an embodiment of the present disclosure.

As shown in FIG. 1, the observation system 1 includes, for example, a lighting device 1100 and an imaging device 1200. Together therewith, FIG. 1 also shows an observation object 1500 to be irradiated with observation light output from the lighting device 1100. The observation system 1 according to the present embodiment can be applied to an imaging system for medical use, such as an endoscope system and a microscope system.

In the observation system 1 according to the present embodiment, it is possible to generate each of white light for normal observation and special light for special observation, and thus possible to obtain, as an observation image, a captured image of the observation object 1500 irradiated with either white light or special light.

Normal observation refers to an observation method for observing the observation object 1500 in a tone close to that of observation with the naked eye under natural light by irradiating the observation object 1500 with white light. For example, it is possible to perform normal observation by irradiating the observation object 1500 with white light and observing the white light reflected from the observation object 1500. The white light is obtained as a result of combining light of different wavelength bands emitted from a plurality of light sources.

Meanwhile, special observation refers to an observation method that enables the structure of a specific living tissue to be observed more clearly, or enables a specific living tissue to be distinguished from other living tissues, by irradiating the observation object 1500 with light of a specific wavelength band. For example, it is possible to perform special observation as follows. A fluorescent substance or the like is administered to the observation object 1500. The fluorescent substance or the like selectively acts on a specific living tissue. After the administration of the fluorescent substance or the like, the observation object 1500 is irradiated with excitation light of the fluorescent substance, so that fluorescence emitted from the fluorescent substance is observed. In other words, special light for special observation is light in a wavelength band that is narrower than the wavelength band of white light, and includes the excitation wavelength of the fluorescent substance administered to the observation object 1500. For example, light emitted from some of the plurality of light sources for generating white light can form such special light for special observation.

The lighting device 1100 includes a plurality of light sources (a red light source 220R, a green light source 220G, and a blue light source 220B), drive circuits (a red light source drive circuit 221R, a green light source drive circuit 221G, and a blue light source drive circuit 221B), an optical system 200, and a control unit 1120. The plurality of light sources emits light of different wavelength bands. The drive circuits drive the plurality of light sources. The optical system 200 combines the light emitted from the plurality of light sources.

Hereinafter, the red light source 220R, the green light source 220G, and the blue light source 220B are also collectively referred to as light sources 220. In addition, the red light source drive circuit 221R, the green light source drive circuit 221G, and the blue light source drive circuit 221B are also collectively referred to as drive circuits 221.

The light sources 220 are multiple light sources that emit light of different wavelength bands. The respective wavelength bands of the light sources 220 are selected such that white light is generated as a result of combining the light emitted from the light sources 220. The light sources 220 may be, for example, the red light source 220R, the green light source 220G, and the blue light source 220B.

Each of the light sources 220 may include a laser light source. Unlike a lamp light source such as a xenon lamp or a halogen lamp, it is possible to control the quantity of light to be emitted from a laser light source, by controlling a drive current or drive voltage to be applied. In a case where each of the light sources 220 includes a laser light source, the lighting device 1100 can control the light quantity and the like of the light sources 220 more rapidly and precisely.

For example, the red light source 220R may be a red laser light source that emits laser light in a red band (for example, a center wavelength of approximately 638 nm). More specifically, the red light source 220R may be a semiconductor laser such as a GaInP quantum well structure laser diode that emits light in a wavelength band of 630 nm to 645 nm. The green light source 220G may be a green laser light source that emits laser light in a green band (for example, a center wavelength of approximately 532 nm). More specifically, the green light source 220G may be a semiconductor laser that has been wavelength-converted by wavelength conversion elements such as a phosphor and a nonlinear optical element so as to emit light in a wavelength band of 510 nm to 540 nm. The blue light source 220B may be a blue laser light source that emits laser light in a blue band (for example, a center wavelength of approximately 450 nm). More specifically, the blue light source 220B may be a semiconductor laser such as a GaInN quantum well structure laser diode that emits light in a wavelength band of 435 nm to 465 nm.

Note that the wavelength bands of the respective light sources 220 are not limited to a combination of the red band, the green band, and the blue band described above as long as white light can be generated as a result of combining light from the light sources 220. For example, the wavelength bands of the respective light sources 220 may be a combination of a yellow band and a blue band, or may be a combination of a red band, a green band, a blue band, and a yellow band.

Each of the drive circuits 221 drives corresponding one of the light sources 220 on the basis of a drive instruction generated by the control unit 1120.

Specifically, each of the drive circuits 221 includes a circuit capable of adjusting a drive current for corresponding one of the light sources 220. The drive circuits 221 may be, for example, the red light source drive circuit 221R, the green light source drive circuit 221G, and the blue light source drive circuit 221B. For example, the red light source drive circuit 221R, the green light source drive circuit 221G, and the blue light source drive circuit 221B function as follows. The red light source drive circuit 221R drives the red light source 220R on the basis of a drive instruction generated by the control unit 1120. The green light source drive circuit 221G drives the green light source 220G on the basis of a drive instruction generated by the control unit 1120. The blue light source drive circuit 221B drives the blue light source 220B on the basis of a drive instruction generated by the control unit 1120.

The optical system 200 combines red light, green light, and blue light respectively emitted from the red light source 220R, the green light source 220G, and the blue light source 220B to generate white light 300 for normal observation. Furthermore, the optical system 200 combines light emitted from some of the red light source 220R, the green light source 220G, and the blue light source 220B to generate special light for special observation.

For example, the special light for special observation may be any of the red light, green light, or blue light respectively emitted from the red light source 220R, the green light source 220G, or the blue light source 220B. Alternatively, the special light for special observation may be light obtained as a result of combining light emitted from some of the light sources 220 at any given light quantity ratio. Light emitted from some of the red light source 220R, the green light source 220G, and the blue light source 220B forms special light for special observation. Therefore, the special light for special observation is light in a wavelength band narrower than that of the white light 300.

The optical system 200 includes, for example, a mirror 201 and dichroic mirrors 203 and 205.

For example, the red light emitted from the red light source 220R is reflected by the mirror 201 to enter the dichroic mirror 203. Note that the mirror 201 may be a dichroic mirror that reflects red light and transmits light of a wavelength outside the wavelength band of red light.

The dichroic mirror 203 reflects green light and transmits light of a wavelength outside the wavelength band of green light. The green light emitted from the green light source 220G is reflected by the dichroic mirror 203 to enter the dichroic mirror 205. Meanwhile, the red light passes through the dichroic mirror 203. Thus, the red light having passed through the dichroic mirror 203 is combined with the green light reflected by the dichroic mirror 203 to enter the dichroic mirror 205.

The dichroic mirror 205 is a mirror that reflects blue light and transmits light of a wavelength outside the wavelength band of blue light. The blue light emitted from the blue light source 220B is reflected by the dichroic mirror 205. Meanwhile, the red light and the green light pass through the dichroic mirror 205. Thus, the red light and the green light having passed through the dichroic mirror 205 are combined with the blue light reflected by the dichroic mirror 205 to form the white light 300. As a result, light emitted from the respective light sources 220 can be combined to generate the white light 300 in the optical system 200. For example, the combined white light 300 is guided by a light guide member, such as an optical fiber, to be applied to the observation object 1500.

The control unit 1120 is an arithmetic processing unit that controls the driving of each of the light sources 220 (the red light source 220R, the green light source 220G, and the blue light source 220B). Specifically, the control unit 1120 calculates a drive current to be applied to each of the light sources 220, on the basis of a target light quantity. Then, the control unit 1120 outputs a drive instruction based on the calculated drive current to each of the drive circuits 221 (the red light source drive circuit 221R, the green light source drive circuit 221G, and the blue light source drive circuit 221B).

For example, the control unit 1120 may store in advance the correlation between the drive current for each of the light sources 220 and the quantity of light to be emitted from each of the light sources 220 by the drive current, and calculate each drive current for achieving the target light quantity on the basis of the correlation. Furthermore, the optical system 200 may include a photodetector that splits light emitted from each of the light sources 220 and detects the split light. The control unit 1120 can determine the quantity of light actually emitted by each of the light sources 220 from the quantity of light detected by the photodetector. It is thus possible to output a drive instruction to each drive circuit such that the quantity of light from each of the light sources 220 is equal to the target light quantity.

Here, in the special observation, a living tissue emphasized with the fluorescence of a fluorescent substance is observed by means of the imaging device 1200. Then, there is a possibility that, with the passage of time, the fluorescent substance administered to the observation object 1500 is diffused and photobleached (photochemical destruction of the fluorescent substance), and that the intensity of the emitted fluorescence decreases. In such a case, the luminance of a pixel corresponding to the fluorescence emitted from the fluorescent substance gradually decreases in a captured image with the passage of time. As a result, the visibility of the captured image decreases.

In the present embodiment, the control unit 1120 controls the quantity of special light so as to maintain the luminance of a captured image of the observation object 1500 irradiated with the special light, at a substantially constant level on the basis of the luminance of the captured image. Specifically, the control unit 1120 controls the quantity of special light on the basis of the luminance of a pixel such that the luminance of the pixel falls within a predetermined range in the captured image of the observation object 1500 irradiated with the special light. The pixel corresponds to the fluorescence emitted from the fluorescent substance excited by the special light.

For example, assume that the fluorescent substance administered to the observation object 1500 is a fluorescein compound having a maximum excitation wavelength near 490 nm and a maximum fluorescence wavelength near 520 nm. In such a case, the control unit 1120 outputs, to the drive circuit 221, a drive instruction to generate special light including blue light that can excite the fluorescein compound. Thereafter, the control unit 1120 outputs, to the drive circuit 221, a drive instruction to control the quantity of special light on the basis of the luminance of a green pixel such that the luminance of the green pixel falls within a predetermined range (that is, the luminance thereof is maintained at a substantially constant level) in the captured image of the observation object 1500 irradiated with the special light. The green pixel corresponds to the fluorescence maximum wavelength of the fluorescein compound.

For example, assume that the highest value or average value of the luminance of the green pixels in the entire captured image of the observation object 1500 irradiated with the special light falls below the predetermined range. In such a case, the control unit 1120 may output, to the blue light source drive circuit 221B, a drive instruction to increase the quantity of the special light including blue light by a predetermined quantity.

However, stronger special light (excitation light) may further accelerate photobleaching of the fluorescent substance. Furthermore, stronger special light may cause the observation object 1500 to be damaged by heat. Moreover, time degradation may be accelerated in the light source 220 that emits stronger special light. Therefore, even in the case of increasing the quantity of special light, it is desirable for the control unit 1120 to maintain the light quantity at or below a certain level where the fluorescent substance, the observation object, the light source 220, or the like is less damaged.

In a case where the quantity of light to be emitted from the light source 220 cannot be increased due to the above-described reasons or the like, the observation system 1 may increase the luminance of pixels of a captured image by, for example, processing the captured image with respect to an S/N ratio, brightness, contrast, sharpness, or the like.

Note that in a case where only light in a wavelength band corresponding to the fluorescence of the fluorescein compound is photoelectrically converted by a band-pass filter in the imaging device 1200, the luminance of all the pixels of the captured image reflects the intensity of the fluorescence of the fluorescein compound. In such a case, the control unit 1120 may output, to the drive circuit 221, a drive instruction to control the quantity of the special light such that the highest value or average value of the luminance of all the pixels of the captured image of the observation object 1500 irradiated with the special light falls within a predetermined range (that is, the highest value or average value thereof is maintained at a substantially constant level).

This enables a user to perform special observation of the observation object 1500 to which a fluorescent substance has been administered, without concern for the possibility that the intensity of fluorescence emitted from the fluorescent substance decreases with the passage of time. Therefore, the observation system 1 can improve user convenience in the special observation.

The imaging device 1200 captures an image of the observation object 1500 irradiated with white light or special light, and obtains a captured image of the observation object 1500. Specifically, the imaging device 1200 includes an imaging element, and obtains a captured image of the observation object 1500 by photoelectrically converting light from the observation object 1500. The imaging element included in the imaging device 1200 may be, for example, a known imaging element capable of color imaging, such as a charge coupled device (CCD) image sensor or a complementary metal-oxide-semiconductor (CMOS) image sensor.

For example, the imaging device 1200 may obtain a captured image for normal observation by photoelectrically converting light reflected from the observation object 1500 irradiated with white light for normal observation. The imaging device 1200 may obtain a captured image for special observation by photoelectrically converting fluorescence emitted from the observation object 1500 irradiated with the special light for special observation. Furthermore, the imaging device 1200 may obtain a moving image indicating temporal changes of the observation object 1500 by continuously obtaining captured images of the observation object 1500 at short intervals (for example, at intervals of 1/30 seconds).

Here, the observation system 1 according to the present embodiment may obtain respective captured images for normal observation and special observation by irradiating the observation object 1500 with white light for normal observation and special light for special observation in a time-division manner. In such a case, the observation system 1 can simultaneously present a user with the respective captured images for normal observation and special observation.

Figure 2:
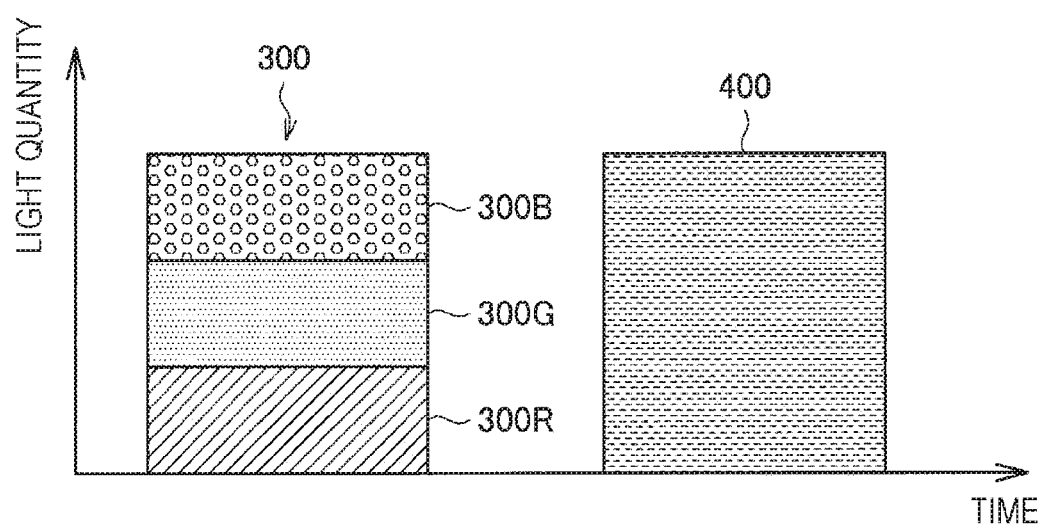
FIG. 2 is a graph showing time-division irradiation with white light for normal observation and special light for special observation.

For example, as shown in FIG. 2, white light and special light can be generated in a time-division manner to be applied to the observation object 1500. FIG. 2 is a graph showing time-division irradiation with white light for normal observation and special light for special observation.

Specifically, the observation system 1 can irradiate the observation object 1500 with the white light 300 and a special light 400 in a time-division manner by applying the white light 300 and the special light 400 in a pulse form only for a certain period of time. The white light 300 is generated as a result of combining red light 300R, green light 300G, and blue light 300B respectively emitted from the red light source 220R, the green light source 220G, and the blue light source 220B. The special light 400 (for example, the blue light 300B emitted from the blue light source 220B) is emitted from some of the red light source 220R, the green light source 220G, and the blue light source 220B.

Note that the ratio of the respective quantities of the red light 300R, the green light 300G, and the blue light 300B in the white light 300 can be appropriately controlled so as to achieve a color temperature close to that of natural light and higher color rendering properties. Note that the light quantity and irradiation time of each of the white light 300 and the special light 400 are appropriately controlled in accordance with observation conditions and the like. Thus, the light quantity and irradiation time of the white light 300 need not be equal to those of the special light 400.

Furthermore, the observation system 1 may capture each image of the observation object 1500 irradiated with white light or special light by, for example, switching light to be applied to the observation object 1500 to white light or special light at each imaging timing of the imaging device 1200. The observation system 1 may capture an image of the observation object 1500 irradiated with white light or special light by, for example, switching light to be applied to the observation object 1500 to white light or special light alternately at intervals of a few seconds. The observation system 1 may capture an image of the observation object 1500 irradiated with white light or special light by, for example, switching light to be applied to the observation object 1500 to white light or special light on the basis of an input from a user.

Moreover, in a case where the imaging device 1200 captures images of the observation object 1500 as a continuous moving image, the control unit 1120 may alternately switch light to be applied to the observation object 1500 to white light or special light every imaging frame or every two or more imaging frames. The time of one imaging frame in a moving image is, for example, 1/30 seconds or 1/60 seconds. Therefore, it is possible for the observation system 1 to capture both images for normal observation and special observation without causing a user to be aware thereof, by switching light to be applied to the observation object 1500 to white light or special light in units of imaging frames.

The observation system 1 according to the present embodiment controls which of the light sources 220 emits light to be used. As a result, there are emitted white light for normal observation and special light for special observation which are different from each other in wavelength spectrum. Thus, each of the light sources 220 will be turned on or off as appropriate depending on whether to generate white light or special light. Here, it is possible to more quickly and precisely control the output of a laser light source and turn on and off the laser light source than a lamp light source. Therefore, in a case where each of the light sources 220 is a laser light source, the observation system 1 can reduce the effect of turning on and off each of the light sources 220 on light quantity, and the like. In such a circumstance, even in the case of alternately generating white light and special light, the observation system 1 can control the light quantities of the white light and the special light independently of each other.

<2. Operation Example of Observation System>

Figure 3:
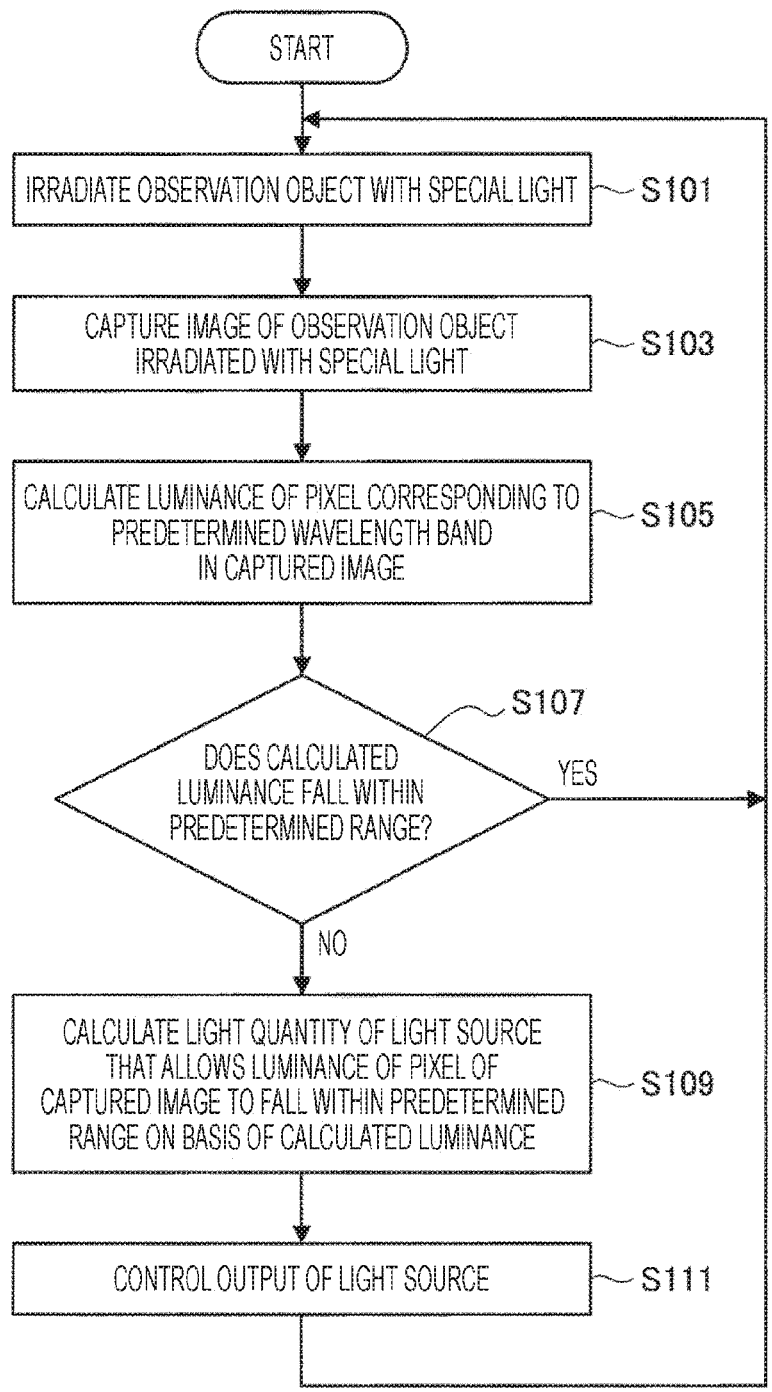
FIG. 3 is a flowchart describing an example of operation in the observation system according to the embodiment.

Next, an operation example of the observation system 1 according to the present embodiment will be described with reference to FIG. 3. Specifically, the following describes operation related to a configuration in which the quantity of special light is controlled on the basis of the luminance of a pixel of a captured image in the observation system 1 according to the present embodiment. FIG. 3 is a flowchart describing an example of the operation in the observation system 1 according to the present embodiment.

As shown in FIG. 3, the lighting device 1100 first generates special light with light emitted from some of the plurality of light sources 220, and irradiates the observation object 1500 with the generated special light (S101). Next, the imaging device 1200 captures an image of the observation object 1500 irradiated with the special light (S103). Subsequently, the control unit 1120 calculates the luminance of a pixel corresponding to a predetermined wavelength band in the captured image (S105). Note that the control unit 1120 may calculate the average value of the luminance of the pixels in the entire captured image, or may calculate the highest value of the luminance of the pixels in the entire captured image.

Here, the predetermined wavelength band refers to the wavelength band of fluorescence to be emitted from the fluorescent substance administered to the observation object 1500. For example, in a case where the predetermined wavelength band falls within a range of 380 nm to 495 nm, the control unit 1120 may select a blue pixel as a pixel corresponding to the predetermined wavelength band, and calculate the luminance of the blue pixel from the captured image. Alternatively, in a case where the predetermined wavelength band falls within a range of 495 nm to 590 nm, the control unit 1120 may select a green pixel as a pixel corresponding to the predetermined wavelength band, and calculate the luminance of the green pixel from the captured image. Alternatively, in a case where the predetermined wavelength band falls within a range of 590 nm to 750 nm, the control unit 1120 may select a red pixel as a pixel corresponding to the predetermined wavelength band, and calculate the luminance of the red pixel from the captured image.

Next, the control unit 1120 determines whether or not the calculated luminance of the pixel falls within a predetermined luminance range (S107). Here, the predetermined luminance range refers to a luminance range in which a less burden is placed on the vision of a user performing special observation. In a case where the calculated luminance of the pixel falls within the predetermined luminance range (S107/Yes), the observation system 1 returns to S101 to irradiate the observation object 1500 with special light (S101), and then captures an image of the observation object 1500 (S103).

Meanwhile, in a case where the calculated luminance of the pixel does not fall within the predetermined luminance range (S107/No), the control unit 1120 determines the light quantity of the light source 220 that allows the luminance of the pixel to fall within the predetermined luminance range in the captured image (S109). Specifically, in a case where the luminance of the pixel of the captured image falls below the predetermined luminance range, the control unit 1120 outputs a drive instruction to drive the light source 220 such that the quantity of special light increases. Alternatively, in a case where the luminance of the pixel of the captured image exceeds the predetermined luminance range, the control unit 1120 outputs a drive instruction to drive the light source 220 such that the quantity of special light decreases. Subsequently, the drive circuit 221 controls the output of the light source 220 that generates special light, on the basis of the drive instruction output from the control unit 1120 (S111). Thereafter, the observation system 1 returns to S101 to irradiate the observation object 1500 with special light (S101), and then captures an image of the observation object 1500 (S103).

According to the operation example above, the observation system 1 according to the present embodiment can control the quantity of special light to be applied to the observation object 1500 such that fluorescence to be emitted from the observation object 1500 falls within a predetermined range in special observation. Thus, although the intensity of the fluorescence to be emitted from the observation object 1500 may vary with the passage of time, the observation system 1 can maintain the intensity of the fluorescence at a substantially constant level. Therefore, the observation system 1 can improve user convenience in the special observation.

<3. Control Patterns of Observation Light>

Subsequently, control patterns of observation light in the observation system 1 according to the present embodiment will be described with reference to FIGS. 4 to 7. FIGS. 4 to 7 are graphs showing examples of the control patterns of observation light in the observation system 1 according to the present embodiment.

As described above, the observation system 1 according to the present embodiment can cause light to switch between white light for normal observation and special light for special observation at any given timing. Therefore, the following describes the switching of white light and special light and the control patterns of light quantity in the observation system 1 according to the present embodiment while taking first to fourth control patterns as examples.

(3.1. First Control Pattern)

First, the first control pattern of the observation system 1 will be described with reference to FIG. 4.

Figure 4:
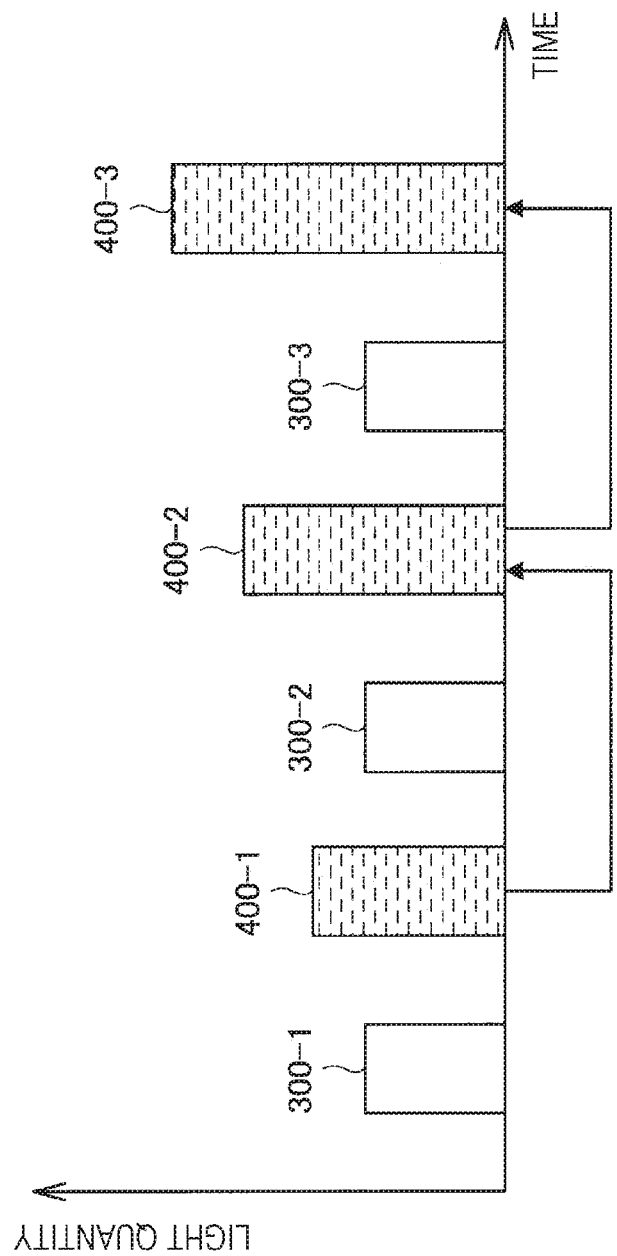
FIG. 4 is a graph showing an example of a control pattern of observation light in the observation system according to the embodiment.

As shown in FIG. 4, in the first control pattern, the observation object 1500 is irradiated with white light for normal observation (white light 300-1, 300-2, 300-3, . . . ) and special light for special observation (special light 400-1, 400-2, 400-3, . . . ) alternately in a pulse form. This enables the observation system 1 to alternately capture an image for normal observation and an image for special observation.

In a case where the observation system 1 captures, as a real-time moving image, images of the observation object 1500 in consecutive frames, the observation system 1 may cause light to switch between white light and special light every frame or every few frames. In such a case, the irradiation time of each of the white light and the special light may be, for example, 1/30 seconds or 1/60 seconds.

Here, the quantity of special light to be applied to the observation object 1500 may be controlled such that the luminance of pixels of a captured image is maintained at a substantially constant level, on the basis of the luminance of pixels of the immediately preceding captured image of the observation object irradiated with the special light. For example, the quantity of the special light 400-2 may be controlled on the basis of the luminance of pixels of a captured image of the observation object 1500 irradiated with the special light 400-1. Similarly, the quantity of the special light 400-3 may be controlled on the basis of the luminance of pixels of a captured image of the observation object 1500 irradiated with the special light 400-2.

It is conceivable that the luminance of pixels of a captured image of the observation object 1500 irradiated with special light gradually decreases due to diffusion of a fluorescent substance, photobleaching, or the like. The observation system 1 can maintain the luminance of the pixels of the captured image of the observation object 1500 at a substantially constant level by appropriately controlling the quantity of special light even in a case where the intensity of fluorescence emitted from the fluorescent substance administered to the observation object 1500 varies.

Meanwhile, the quantities of the white light 300-1, 300-2, and 300-3 to be applied to the observation object 1500 may be constant. It is considered that a captured image of the observation object 1500 irradiated with white light involves less variation in the luminance of pixels than the captured image of the observation object 1500 irradiated with special light. Therefore, the quantities of the white light 300-1, 300-2, and 300-3 need not be variably controlled like the quantities of the special light 400-1, 400-2, and 400-3.

Therefore, according to the first control pattern, a user can simultaneously observe a captured image for normal observation and a captured image for special observation.

(3.2. Second Control Pattern)

Next, the second control pattern of the observation system 1 will be described with reference to FIG. 5.

Figure 5:
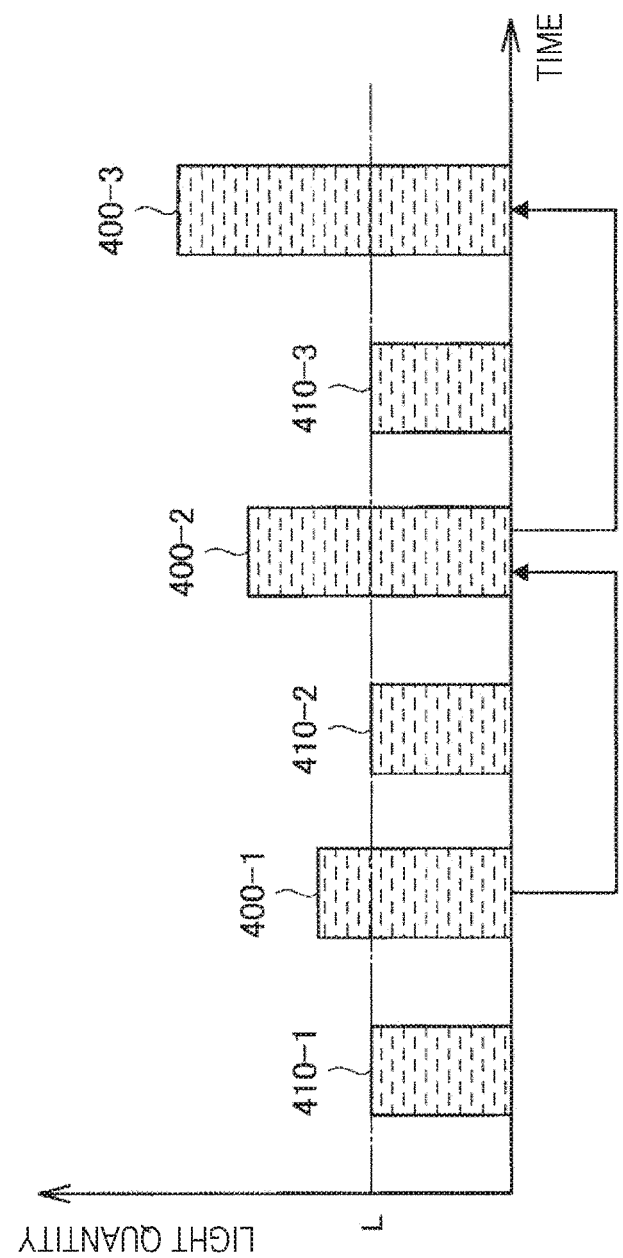
FIG. 5 is a graph showing an example of the control pattern of observation light in the observation system according to the embodiment.

As shown in FIG. 5, in the second control pattern, the observation object 1500 may be irradiated with special light for special observation (410-1, 410-2, 410-3, . . . ) with a constant light quantity and the special light for special observation (400-1, 400-2, 400-3, . . . ) with a variable light quantity, alternately in a pulse form. This enables the observation system 1 to alternately capture an image for special observation reflecting temporal variation in the intensity of fluorescence, and an image for special observation in which the luminance of pixels is maintained at a substantially constant level.

For example, the observation system 1 may alternately irradiate the observation object 1500 with the special light 410-1, 410-2, and 410-3 and the special light 400-1, 400-2, and 400-3. The quantities of the special light 410-1, 410-2, and 410-3 to be applied is maintained at a constant quantity L. The quantities of the special light 400-1, 400-2, and 400-3 to be applied is controlled on the basis of the luminance of pixels of a captured image. In a case where the observation system 1 captures, as a real-time moving image, images of the observation object 1500 in consecutive frames, the observation system 1 may cause light to switch between the special light for special observation with a constant light quantity and the special light for special observation with a variable light quantity, every frame or every few frames.

Note that the irradiation time of each special light may be, for example, 1/30 seconds or 1/60 seconds.

This is because it is possible that temporal changes of the intensity of fluorescence emitted from the observation object 1500 may be observed depending on the purpose, conditions, or the like of observation. In such a case, it is preferable for the observation system 1 to maintain the quantity of special light to be applied to the observation object 1500 at a constant level such that the intensity of fluorescence emitted from the observation object 1500 is reflected in the luminance of pixels of a captured image.

Meanwhile, it is preferable to maintain the luminance of the pixels of the captured image at a substantially constant level for the purpose of observing a portion of the observation object 1500, at which fluorescence is emitted. In such a case, the observation system 1 may control the quantity of special light to be applied to the observation object 1500 such that the luminance of pixels of a captured image is maintained at a substantially constant level, on the basis of the luminance of pixels of a captured image of the observation object irradiated with special light.

For example, the quantity of the special light 400-2 may be controlled on the basis of the luminance of pixels of a captured image of the observation object 1500 irradiated with the special light 400-1. Similarly, the quantity of the special light 400-3 may be controlled on the basis of the luminance of pixels of a captured image of the observation object 1500 irradiated with the special light 400-2.

Note that, needless to say, the quantity of special light may be controlled on the basis of the luminance of pixels of a captured image of the observation object 1500 irradiated with special light other than the special light 400-1, 400-2, and 400-3 with a light quantity variably controlled. For example, the quantity of the special light 400-2 may be controlled on the basis of the luminance of pixels of a captured image of the observation object 1500 irradiated with the special light 410-2, which is the immediately preceding captured image.

In such a case, it is desirable for the observation system 1 to allow a user to refer later to the luminance of the relevant one of observation images on the basis of which the quantity of special light to be applied has been controlled. For example, the observation system 1 may cause an image of the observation object 1500 to be stored in association with a mode in which the quantity of special light to be applied to the observation object 1500 has been controlled at the time of capturing the image. More specifically, the observation system 1 may cause information regarding the way how the quantity of special light to be applied to the observation object 1500 has been controlled at the time of capturing the image, to be stored as embedded information in the image of the observation object 1500.

Therefore, according to the second control pattern, it is possible for a user to simultaneously observe observation images captured for different observation purposes by irradiation with special light of different light quantities.

(3.3. Third Control Pattern)

Subsequently, the third control pattern of the observation system 1 will be described with reference to FIG. 6.

Figure 6:
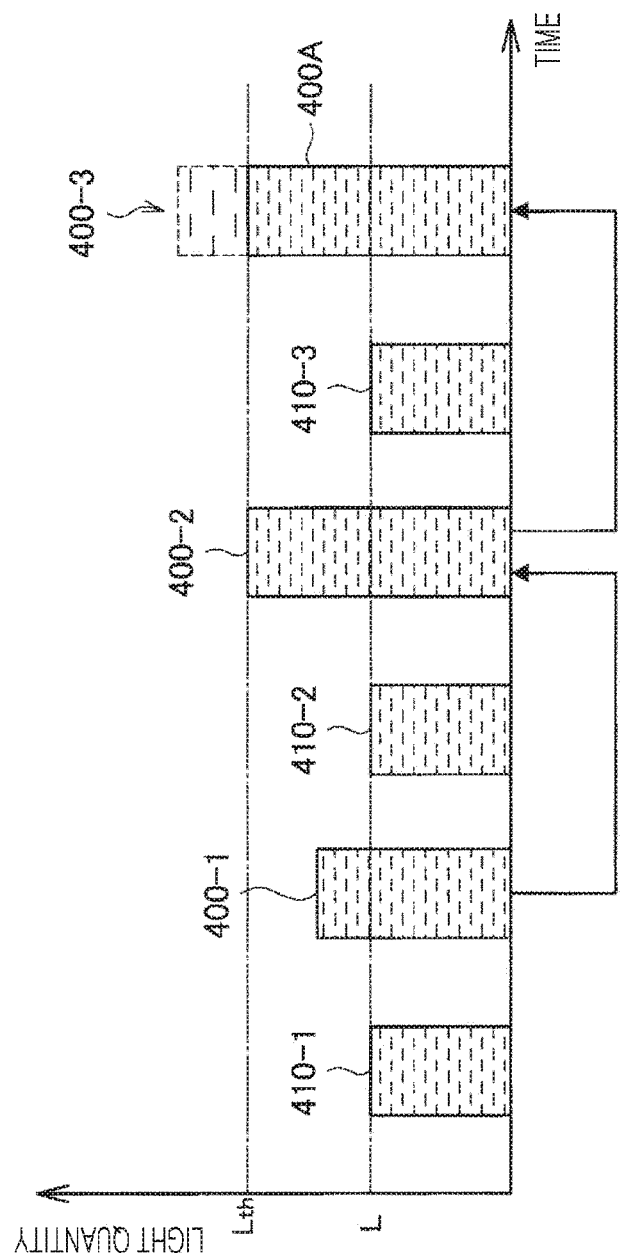
FIG. 6 is a graph showing an example of the control pattern of observation light in the observation system according to the embodiment.

As shown in FIG. 6, in the third control pattern, the observation object 1500 may be irradiated with the special light for special observation (410-1, 410-2, 410-3, . . . ) with a constant light quantity and the special light for special observation (400-1, 400-2, 400-3, . . . ) with a variable light quantity, alternately in a pulse form as in the second control pattern. However, the third control pattern is different from the second control pattern in that the upper limit of the quantity of special light is set so that the quantity of special light does not exceed a threshold $L_{th}$. This enables the observation system 1 to prevent an excessive burden from being placed on the observation object 1500, the fluorescent substance administered to the observation object 1500, the light source 220, and the like as a result of irradiating the observation object 1500 with an excessive quantity of special light.

For example, the observation system 1 may alternately irradiate the observation object 1500 with the special light 410-1, 410-2, and 410-3 and the special light 400-1, 400-2, and 400-3. The quantities of the special light 410-1, 410-2, and 410-3 to be applied is maintained at a constant quantity L. The quantities of the special light 400-1, 400-2, and 400-3 to be applied is controlled on the basis of the luminance of pixels of a captured image. Here, in a case where the quantity of the special light 400-3 calculated on the basis of the luminance of pixels of a captured image exceeds the threshold $L_{th}$, the observation system 1 controls the quantity of the special light 400-3 to be applied to the observation object 1500 so that the quantity of the special light 400-3 falls below the threshold $L_{th}$. Accordingly, the observation object 1500 is irradiated with special light 400A with a light quantity reduced to a value equal to or less than the threshold $L_{th}$.

In such a case, the observation system 1 may perform image processing on a captured observation image to maintain the luminance of pixels of the observation image at a substantially constant level. For example, the observation system 1 may maintain the luminance of the pixels of the observation image at a substantially constant level by controlling the S/N ratio, brightness, contrast, sharpness, or the like of the captured image.

Therefore, according to the third control pattern, a user can perform special observation without placing an excessive burden on the observation object 1500, the fluorescent substance administered to the observation object 1500, the light source 220, and the like.

(3.4. Fourth Control Pattern)

Next, the fourth control pattern of the observation system 1 will be described with reference to FIG. 7.

Figure 7:
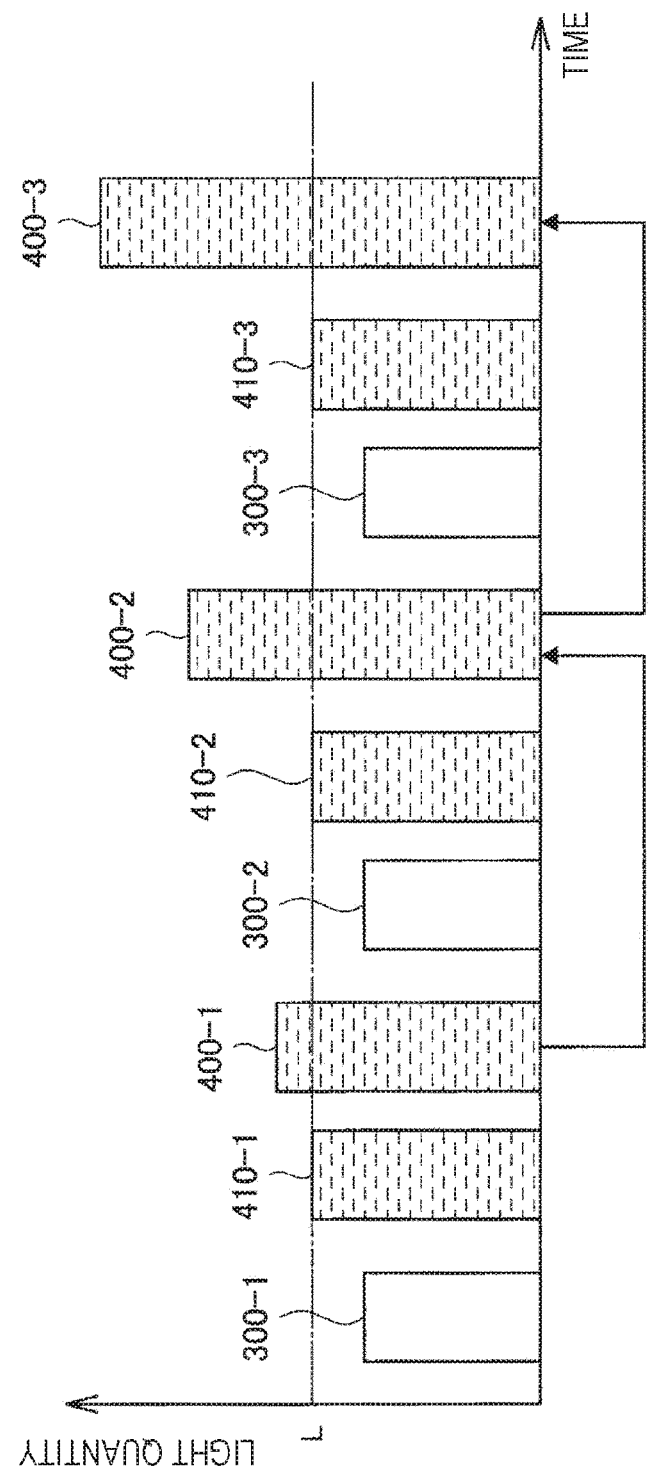
FIG. 7 is a graph showing an example of the control pattern of observation light in the observation system according to the embodiment.

As shown in FIG. 7, in the fourth control pattern, the observation object 1500 may be irradiated, in turn, with the white light for normal observation (the white light 300-1, 300-2, 300-3, . . . ), the special light for special observation (410-1, 410-2, 410-3, . . . ) with a constant light quantity, and the special light for special observation (400-1, 400-2, 400-3, . . . ) with a variable light quantity, in a pulse form. This enables the observation system 1 to capture, in turn, images of the observation object 1500 irradiated with light with varied wavelength spectra, light quantities, and the like.

For example, the observation system 1 may irradiate the observation object 1500, in turn, with the white light 300-1, 300-2, and 300-3 for normal observation, the special light 410-1, 410-2, and 410-3, and the special light 400-1, 400-2, and 400-3. The quantity of the special light 410-1, 410-2, and 410-3 to be applied is maintained at the constant quantity L. The quantity of the special light 400-1, 400-2, and 400-3 to be applied is controlled on the basis of the luminance of pixels of a captured image.

In a case where the observation system 1 captures, as a real-time moving image, images of the observation object 1500 in consecutive frames, the observation system 1 may cause light to switch between the white light for normal observation, the special light for special observation with a constant light quantity, and the special light for special observation with a variable light quantity, every frame or every few frames. In such a case, the irradiation time of each light may be, for example, 1/30 seconds or 1/60 seconds.

In a case where the light sources 220 are laser light sources, it is possible, in the observation system 1 according to the present embodiment, to quickly turn on and off each of the light sources 220 and control the light quantity of each of the light sources 220 without considering temporal variation in light quantity and the like due to state transition. Therefore, the observation system 1 can irradiate the observation object 1500 with various types of light having varied wavelength spectra, light quantities, and the like.

Note that the quantity of the special light 400-2 may be controlled on the basis of the luminance of pixels of a captured image of the observation object 1500 irradiated with the special light 400-1. Similarly, the quantity of the special light 400-3 may be controlled on the basis of the luminance of pixels of a captured image of the observation object 1500 irradiated with the special light 400-2. Alternatively, as described in the third control pattern, the quantity of special light may be controlled on the basis of the luminance of pixels of a captured image of the observation object 1500 irradiated with special light other than the special light 400-1, 400-2, and 400-3 with a light quantity variably controlled. For example, the quantity of the special light 400-2 may be controlled on the basis of the luminance of pixels of a captured image of the observation object 1500 irradiated with the special light 410-2, which is the immediately preceding captured image.

Therefore, according to the fourth control pattern, a user can simultaneously observe images of the observation object 1500 irradiated with light having different wavelength spectra, light quantities, and the like.

<4. Specific Example of Observation System>

Figure 8:
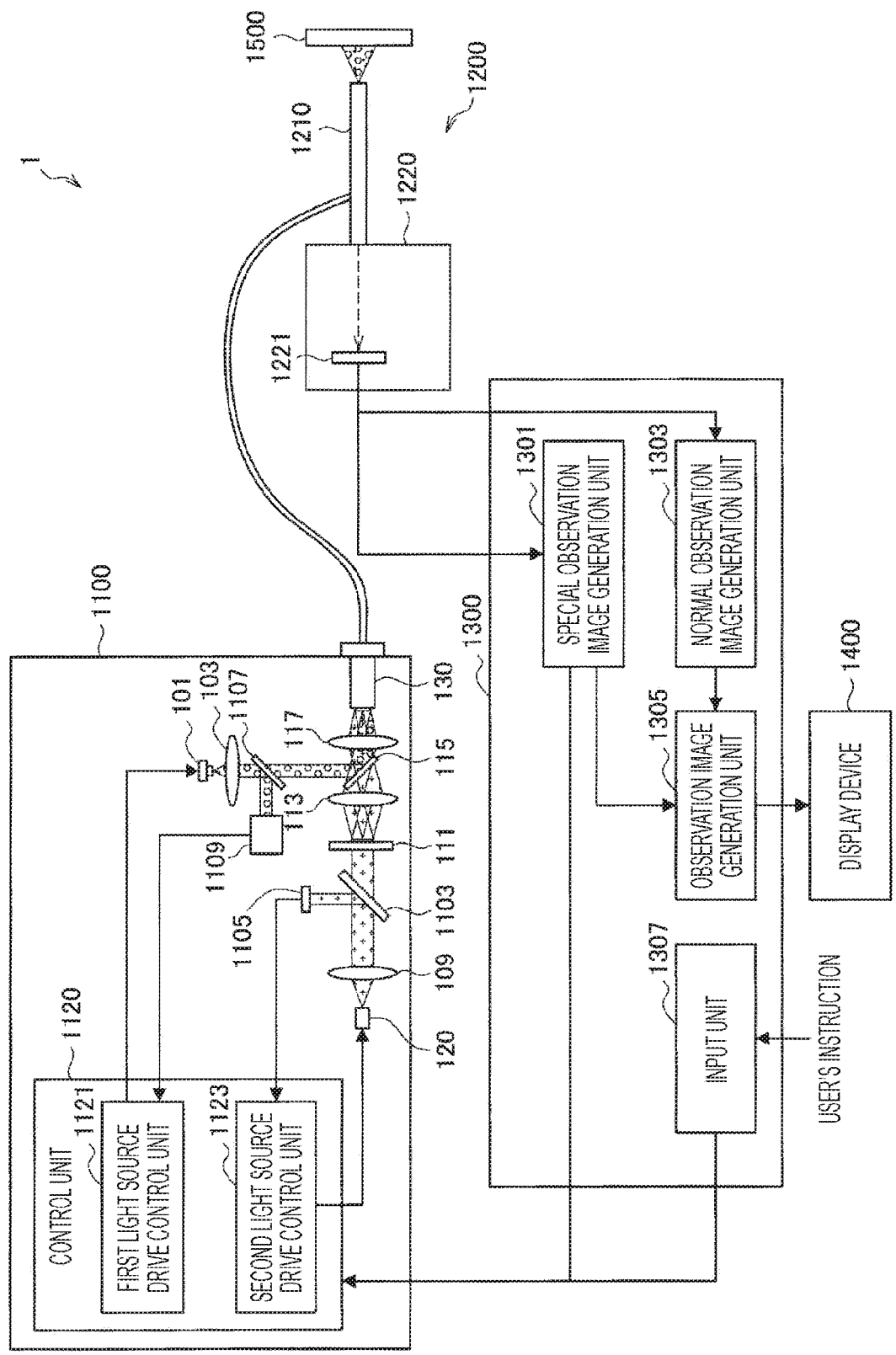
FIG. 8 is a schematic diagram showing a specific configuration example of the observation system according to the embodiment.

Subsequently, a more specific configuration example of the observation system 1 according to the embodiment of the present disclosure will be described with reference to FIG. 8. FIG. 8 is a schematic diagram showing a specific configuration example of the observation system 1 according to the present embodiment.

As shown in FIG. 8, the observation system 1 includes the lighting device 1100, the imaging device 1200, an information processing device 1300, and a display device 1400. Note that together therewith, FIG. 8 also shows the observation object 1500 to be irradiated with observation light output from the lighting device 1100.

(Lighting Device 1100)

The lighting device 1100 includes a first light source 101, a first collimating optical system 103, a first half mirror 1107, a first photodetector 1109, the control unit 1120, a second light source 120, a second collimating optical system 119, a second half mirror 1103, a second photodetector 1105, a diffusion member 111, a third collimating optical system 113, a dichroic mirror 115, and a condenser optical system 117. The second light source 120 corresponds to, for example, the light source 220 shown in FIG. 1. The control unit 1120 corresponds to the control unit 1120 shown in FIG. 1.

Light emitted from the first light source 101 passes through the first collimating optical system 103. As a result, the emitted light turns into substantially parallel light to be incident on the dichroic mirror 115. Furthermore, a part of the light emitted from the first light source 101 is split by the first half mirror 1107, and enters the first photodetector 1109. Meanwhile, light emitted from the second light source 120 passes through, in order, a second collimating optical system 109, the diffusion member 111, and the third collimating optical system 113 to turn into substantially parallel light, and enters the dichroic mirror 115. Furthermore, a part of the light emitted from the second light source 120 is split by the second half mirror 1103, and enters the second photodetector 1105. The dichroic mirror 115 combines the light emitted from the first light source 101 and the light emitted from the second light source 120. The combined light, as observation light, enters a light guide 130 through the condenser optical system 117.

The first light source 101 includes, for example, a white light source, and emits white light. The type of the white light source to be included in the first light source 101 is not particularly limited. However, the first light source 101 may include, for example, a white light emitting diode (LED), a laser-excited phosphor, a xenon lamp, a halogen lamp, or the like. Specifically, the first light source 101 may include a so-called phosphor-type white LED using a phosphor excited by a blue LED.

In the observation system 1 according to the present embodiment, the first light source 101 is an optional constituent element, and need not be included in the observation system 1 in some cases. However, in a case where the observation system 1 includes the first light source 101, the observation system 1 can generate white light for normal observation by using light emitted from the white light source. It is thus possible to improve the color rendering properties of white light for normal observation. The observation system 1 including the first light source 101 as described above can make the tone of a captured image of an observation object at the time of normal observation closer to the tone of observation with the naked eye under natural light.

Note that the observation system 1 according to the present embodiment may further include, as a third light source, a light source that emits light outside the visible light band. Specifically, the observation system 1 may include, as the third light source, a light source that emits light in the near-infrared band, a light source that emits light in the ultraviolet band, or the like. As a result of including the third light source as described above, the observation system 1 can increase the types of usable fluorescent substance. For example, it becomes possible for the observation system 1 to use indocyanine green (ICG) or 5-aminolevulinic acid (5-ALA), as a fluorescent substance. The indocyanine green (ICG) has an excitation wavelength in the near-infrared band. The 5-aminolevulinic acid (5-ALA) has an excitation wavelength in the ultraviolet band.

The first collimating optical system 103 converts the white light emitted from the first light source 101 into a parallel light flux, and causes the parallel light flux to be incident on the dichroic mirror 115 from a direction different from that of light having passed through the third collimating optical system 113 (for example, from a direction that allows the optical axes of the parallel light flux and the light having passed through the third collimating optical system 113, to be substantially orthogonal to each other). Light having passed through the first collimating optical system 103 need not be a perfect parallel beam, and just needs to be diverging light close to a parallel beam.

The first half mirror 1107 is provided between, for example, the first light source 101 and the dichroic mirror 115, and splits a part of the light emitted from the first light source 101. The split light enters the first photodetector 1109. The first half mirror 1107 is an example of a branching member. Thus, another branching member may be used instead of the first half mirror 1107.

The first photodetector 1109 detects the quantity of the light emitted from the first light source 101, and outputs the detected light quantity to a first light source drive control unit 1121. As a result, the first light source drive control unit 1121 can control the quantity of light to be emitted from the first light source 101 on the basis of, for example, the detected light quantity. The first photodetector 1109 may include, for example, a known photodetector such as a photodiode or a color sensor.

The second light source 120 includes a plurality of light sources that emits light of different wavelength bands. The wavelength bands of the plurality of light sources included in the second light source 120 are selected such that white light is generated as a result of combining emitted light.

Specifically, the second light source 120 may include a plurality of laser light sources that emits light of different wavelength bands. Unlike a lamp light source such as a xenon lamp or a halogen lamp, it is possible to control the quantity of light to be emitted from a laser light source, by controlling a drive current or drive voltage to be applied. As a result of including the laser light sources, the second light source 120 can more rapidly and precisely control light quantity and the like.

However, the second light source 120 may include another type of light source other than a laser light source, as long as light quantity and the like can be electrically controlled. Note that the diffusion of light emitted from a laser light source is small. Therefore, in a case where the second light source 120 includes a plurality of laser light sources, the second photodetector 1105 to be described later can more easily detect the light quantity of the second light source 120.

The second collimating optical system 109 converts the light emitted from the second light source 120 (that is, white light generated as a result of combining light from the respective laser light sources included in the second light source 120, or special light including light from some of the laser light sources included in the second light source 120) into a parallel light flux. The second collimating optical system 109 converts, into a parallel light flux, light to be incident on the diffusion member 111 provided at a subsequent stage. As a result, the second collimating optical system 109 enables the diffusion member 111 to easily control the diffusion state of light. Light having passed through the second collimating optical system 109 need not be a perfect parallel beam, and just needs to be diverging light close to a parallel beam.

The second half mirror 1103 is provided between, for example, the second collimating optical system 109 and the diffusion member 111, and splits a part of the light emitted from the second light source 120. The light split by the second half mirror 1103 enters the second photodetector 1105. The second half mirror 1103 is an example of a branching member. Thus, another branching member may be used instead of the second half mirror 1103.

The second photodetector 1105 detects the quantity of the light emitted from the second light source 120, and outputs the detected light quantity to a second light source drive control unit 1123. As a result, the second light source drive control unit 1123 can control the quantity of light to be emitted from the second light source 120 on the basis of, for example, the detected light quantity. The second photodetector 1105 may include, for example, a known photodetector such as a photodiode or a color sensor.

The diffusion member 111 is provided within a range in the vicinity of the focal position of the second collimating optical system 109 (for example, within a range of approximately 10% of a focal distance from the focal position in either direction), and diffuses light emitted from the second collimating optical system 109. As a result, the light emission end of the diffusion member 111 can be regarded as a secondary light source. Light generated as a result of combining light emitted from a plurality of light sources may have variation in the divergence angles of light between the plurality of light sources. Thus, the divergence angles of the combined light may be unified by conversion into the secondary light source through the diffusion member 111.

The size of the secondary light source to be generated by the diffusion member 111 can be controlled by the focal distance of the second collimating optical system 109. Furthermore, the numerical aperture (NA) of light to be emitted from the secondary light source to be generated by the diffusion member 111 can be controlled by the diffusion angle of the diffusion member 111. Thus, it is possible for the diffusion member 111 to independently control both the size of a light collection spot at the time of coupling to the light guide 130, and an incident NA.

The type of the diffusion member 111 is not particularly limited, and various known diffusion elements can be used as the diffusion member 111. For example, the diffusion member 111 may be frosted ground glass, an opal diffuser plate with a light diffusion material dispersed in glass, or a holographic diffuser plate. In particular, with regard to the holographic diffuser plate, it is also possible to arbitrarily set the diffusion angle of outgoing light by a holographic pattern provided on a substrate.

The third collimating optical system 113 converts light from the diffusion member 111 (that is, light from the secondary light source) into a parallel light flux, and causes the parallel light flux to enter the dichroic mirror 115. Note that light having passed through the third collimating optical system 113 need not be a perfect parallel beam, and just needs to be diverging light close to a parallel beam.

The dichroic mirror 115 combines the light emitted from the first light source 101 and the light emitted from the second light source 120, incident from respective directions such that the optical axes are substantially orthogonal to each other.

In the configuration example shown in FIG. 8, the dichroic mirror 115 is designed to transmit only light of a wavelength band corresponding to light to be emitted from the second light source 120, and to reflect light of a wavelength band other than the wavelength band described above. In such a case, the light emitted from the second light source 120 passes through the dichroic mirror 115 to enter the condenser optical system 117. Furthermore, only a part of the light emitted from the first light source 101, corresponding to light in a band other than the wavelength band corresponding to the light from the second light source 120, is reflected by the dichroic mirror 115, and enters the condenser optical system 117. As a result, the dichroic mirror 115 can combine the light emitted from the first light source 101 and the light emitted from the second light source 120.

Note that the dichroic mirror 115 is an example of an optical member that combines the light emitted from the first light source 101 and the light emitted from the second light source 120, and another optical member can be used as the dichroic mirror 115. For example, it is also possible to use, as an optical member, a dichroic prism capable of combining a plurality of light beams having different wavelengths, a polarization beam splitter capable of combining a plurality of light beams having different polarizations, or a beam splitter capable of combining a plurality of light beams having different amplitudes.

The condenser optical system 117 causes the light combined by the dichroic mirror 115 to form an image on the light guide 130 with a predetermined paraxial lateral magnification. The condenser optical system 117 may include, for example, a condenser lens.

The light guide 130 guides light emitted from the lighting device 1100 to a lens barrel 1210 of the imaging device 1200. The light guide 130 may include, for example, an optical fiber. The type of optical fiber included in the light guide 130 is not particularly limited, and a known multi-mode optical fiber (for example, a step-index multimode fiber) can be used. The core diameter of the optical fiber is also not particularly limited. A core diameter of, for example, approximately 1 mm is appropriate for the optical fiber.

Note that in the above-described lighting device 1100, the imaging magnification by the third collimating optical system 113 and the condenser optical system 117 can be set on the basis of (focal distance of the condenser optical system 117)/(focal distance of the third collimating optical system 113). For example, the imaging magnification provided by the third collimating optical system 113 and the condenser optical system 117 is set such that the size and divergence angle of the secondary light source match the core diameter and incident NA of the light guide 130.

The imaging magnification provided by the first collimating optical system 103 and the condenser optical system 117 can be set on the basis of (focal distance of the condenser optical system 117)/(focal distance of the first collimating optical system 103). For example, the imaging magnification provided by the first collimating optical system 103 and the condenser optical system 117 is set such that the light from the first light source 101 matches the core diameter and incident NA of the light guide 130 to achieve coupling to the light guide 130 with high efficiency.

The control unit 1120 is a control circuit that controls each constituent element of the lighting device 1100. Specifically, the control unit 1120 includes the first light source drive control unit 1121 and the second light source drive control unit 1123. The first light source drive control unit 1121 controls the first light source 101. The second light source drive control unit 1123 controls the second light source 120. For example, the control unit 1120 includes a processor such as a central processing unit (CPU), a micro processing unit (MPU), or a digital signal processor (DSP). The control unit 1120 implements various functions by causing the processor to perform arithmetic processing according to a predetermined program.

Specifically, the first light source drive control unit 1121 controls the quantity of light to be output from the first light source 101. For example, the first light source drive control unit 1121 may control the quantity of light to be output from the first light source 101 by controlling a drive current for the first light source 101. The second light source drive control unit 1123 controls the quantity of light to be output from the second light source 120. For example, the second light source drive control unit 1123 may control the quantity of light to be output from the second light source 120 by controlling a drive current for each laser light source included in the second light source 120.

(Imaging Device 1200)

The imaging device 1200 includes the lens barrel 1210 and an imaging unit 1220.

For example, the lens barrel 1210 has rigidity, and is formed in a substantially cylindrical shape. Alternatively, the lens barrel 1210 has flexibility, and is formed in a tube shape. The light guide 130 extending from the lighting device 1100 is introduced into the lens barrel 1210 to guide observation light emitted from the lighting device 1100 to the observation object 1500. Furthermore, the lens barrel 1210 obtains light reflected from the observation object 1500, and guides the light to the imaging unit 1220.

The imaging unit 1220 includes an imaging element 1221, and photoelectrically converts the light from the observation object 1500. The imaging element 1221 is, for example, an imaging element capable of color imaging. A known imaging element such as a CCD image sensor or a CMOS image sensor can be used as the imaging element 1221. The imaging unit 1220 outputs an image signal photoelectrically converted by the imaging element 1221 to the information processing device 1300. For example, the imaging unit 1220 may output an image signal to a special observation image generation unit 1301 and a normal observation image generation unit 1303 to be described later.

Note that the imaging unit 1220 may include an optical filter that transmits only light in a predetermined wavelength band. For example, the optical filter may be a band-pass filter that includes a dielectric multilayer film and transmits only light in a predetermined wavelength band including fluorescence to be emitted from the fluorescent substance administered to the observation object 1500. The use of such an optical filter enables the imaging element 1221 to selectively perform photoelectric conversion of the fluorescence emitted from the fluorescent substance administered to the observation object 1500.

(Information Processing Device 1300)

The information processing device 1300 generates an observation image of the observation object 1500 on the basis of the image signal input from the imaging device 1200. Furthermore, the information processing device 1300 outputs, to the lighting device 1100, a feedback signal to be used to control the light quantity of the lighting device 1100, on the basis of the generated observation image.

Specifically, the information processing device 1300 includes the special observation image generation unit 1301, the normal observation image generation unit 1303, an observation image generation unit 1305, and an input unit 1307. For example, the information processing device 1300 includes a processor such as a CPU, an MPU, or a DSP, or a microcomputer having the processor mounted thereon. The processor performs arithmetic processing according to a predetermined program to implement each function of the information processing device 1300.

The special observation image generation unit 1301 generates an image for special observation of the observation object 1500 on the basis of the image signal output from the imaging element 1221. Specifically, the special observation image generation unit 1301 may generate an image for special observation on the basis of an output signal of a pixel of a color corresponding to the fluorescence emitted from the fluorescent substance administered to the observation object 1500.

For example, fluorescence to be emitted from a fluorescein compound, which is a fluorescent substance, has a maximum wavelength of 521 nm. Therefore, in a case where the imaging element 1221 generates color image signals in three colors of red, green and blue, the imaging element 1221 can photoelectrically convert fluorescence emitted from the fluorescein compound in a pixel where green light is to be photoelectrically converted. In such a case, the special observation image generation unit 1301 can generate an image for special observation by generating a captured image on the basis of an image signal corresponding to green among image signals output from the imaging element 1221.

Note that in a case where the imaging unit 1220 includes a band-pass filter that selectively transmits the fluorescence emitted from the observation object 1500, the color image signal output from the imaging element 1221 reflects the intensity of the fluorescence emitted from the observation object 1500. In such a case, the special observation image generation unit 1301 can generate an image for special observation by generating a captured image on the basis of the image signal output from the imaging element 1221.

The normal observation image generation unit 1303 generates an image for normal observation of the observation object 1500 on the basis of the signal output from the imaging element 1221. Specifically, the normal observation image generation unit 1303 can generate an image for normal observation by generating a color image on the basis of image signals including the three colors of red, green, and blue, output from the imaging element 1221.

The observation image generation unit 1305 generates an observation image including at least one of the image for special observation generated by the special observation image generation unit 1301 or the image for normal observation generated by the normal observation image generation unit 1303. For example, the observation image generated by the observation image generation unit 1305 is output to the display device 1400, so that a user can visually recognize the observation image. The observation image generated by the observation image generation unit 1305 may include either the image for special observation or the image for normal observation described above, or may include both the image for special observation and the image for normal observation. Details of the observation image to be generated by the observation image generation unit 1305 may be determined by, for example, an input from the user via the input unit 1307.

The input unit 1307 is an input interface that receives a user's operation input. For example, the input unit 1307 includes input devices to be operated by a user, such as a mouse, a keyboard, a touch panel, a button, a switch, and a lever. A user can input various types of information or instructions to the observation system 1 by operating the input unit 1307.

The input unit 1307 may input, to the observation system 1, a signal indicating whether to perform the normal observation, the special observation, or both the normal observation and the special observation. This enables a user to input, to the observation system 1, an instruction as to whether to select a normal observation mode, a special observation mode, or a normal/special observation mode (a mode for simultaneously performing the normal observation and the special observation). Information selected by the user is input to the observation image generation unit 1305 as well as the first light source drive control unit 1121 and the second light source drive control unit 1123 of the lighting device 1100. As a result, the first light source drive control unit 1121 and the second light source drive control unit 1123 respectively drive the first light source 101 and the second light source 120 on the basis of the selected observation mode. Furthermore, the observation image generation unit 1305 generates an observation image on the basis of the selected observation mode.

(Display Device 1400)

The display device 1400 displays the image generated by the observation image generation unit 1305 of the information processing device 1300. For example, the display device 1400 may be a known display device such as a CRT display device, a liquid crystal display device, a plasma display device, or an EL display device. A user can diagnose or treat the observation object 1500 by visually recognizing the image displayed on the display device 1400.

The observation system 1 having the configuration above can be used as, for example, an endoscope apparatus or a microscope apparatus.

<5. Supplementary Notes>

Although the preferred embodiment of the present disclosure has been described above in detail with reference to the accompanying drawings, the technical scope of the present disclosure is not limited to such an example. It will be apparent to a person having ordinary skill in the art of the present disclosure that various modifications or alterations can be conceived within the scope of the technical idea described in the claims. It is understood that, of course, such modifications or alterations are also within the technical scope of the present disclosure.

Furthermore, the effects described in the present specification are merely explanatory or illustrative, and not restrictive. That is, the technology according to the present disclosure can achieve other effects obvious to those skilled in the art from descriptions in the present specification, together with or instead of the above-described effects.

Note that the following configurations are also within the technical scope of the present disclosure.

(1)

An observation system including:

a plurality of light sources that emits light of different wavelength bands that can be combined to generate white light;

an optical system that irradiates an observation object with first light that includes light emitted from some of the plurality of light sources;

an imaging device that captures an image of the observation object irradiated with the first light; and a light source control unit that controls a quantity of the first light on the basis of a luminance of a pixel corresponding to a predetermined wavelength band in the captured image.

(2)

The observation system according to (1) above, in which the light source control unit controls the quantity of the first light such that a value of the luminance of the pixel falls within a predetermined range.

(3)

The observation system according to (2) above, in which the optical system combines the light emitted from the plurality of light sources to generate second light which is white light, and irradiates the observation object with the second light.

(4)

The observation system according to (3) above, in which the light source control unit switches light to be applied to the observation object to the first light or the second light in a time-division manner.

(5)

The observation system according to (4) above, in which the imaging device continuously captures images of the observation object, and the light source control unit switches the light to be applied to the observation object for each of the captured images.

(6)

The observation system according to any one of (2) to (5) above, in which the light source control unit switches, in a time-division manner, the quantity of the first light to be applied to the observation object to a constant light quantity or a light quantity controlled on the basis of the luminance of the pixel corresponding to the predetermined wavelength band in the captured image.

(7)

The observation system according to (6) above, in which the captured image is associated with a quantity of the first light applied to the observation object at a time of capturing the image.

(8)

The observation system according to any one of (2) to (7) above, in which in a case where the quantity of the first light that allows the value of the luminance of the pixel to fall within the predetermined range exceeds a threshold, the light source control unit controls the quantity of the first light such that the quantity of the first light is equal to the threshold.

(9)

The observation system according to any one of (1) to (8) above, in which the plurality of light sources is a plurality of laser light sources.

(10)

The observation system according to (9) above, in which the plurality of light sources includes a red light source, a green light source, and a blue light source.

(11)

The observation system according to any one of (1) to (10) above, further including:

a white light source that emits white light.

(12)

The observation system according to any one of (1) to (11) above, further including:

a special light source that emits light of a wavelength band different from any of the wavelength bands of the plurality of light sources.

(13)

A light source control apparatus including:

a light source control unit that controls a quantity of first light to be applied to an observation object on the basis of a luminance of a pixel corresponding to a predetermined wavelength band in a captured image of the observation object, in which the first light includes light emitted from some of a plurality of light sources that emits light of different wavelength bands that can be combined to generate white light.

REFERENCE SIGNS LIST

1 Observation system
200 Optical system
201 Mirror
203 Dichroic mirror
205 Dichroic mirror
220B Blue light source
220G Green light source
220R Red light source
221B Blue light source drive circuit
221G Green light source drive circuit
221R Red light source drive circuit
300 White light
400 Special light
1100 Lighting device
1120 Control unit
1200 Imaging device
1500 Observation object

The invention claimed is:

1. An observation system comprising:
a plurality of light sources that emit light of different wavelength bands that can be combined to generate white light;
an optical system that irradiates an observation object with first light that includes light emitted from some of the plurality of light sources, combines the light emitted from the plurality of light sources to generate second light which is white light, and irradiates the observation object with the second light;
an imaging device that captures an image of the observation object irradiated with the first light; and
light source control circuitry configured to control a quantity of the first light on a basis of a luminance of a pixel corresponding to a predetermined wavelength band in the captured image such that a value of the luminance of the pixel falls within a predetermined range.

2. The observation system according to claim 1, wherein the light source control circuitry switches light to be applied to the observation object to the first light or the second light in a time-division manner.

3. The observation system according to claim 2, wherein the imaging device continuously captures images of the observation object, and
the light source control circuitry switches the light to be applied to the observation object for each of the captured images.

4. The observation system according to claim 1, wherein the light source control circuitry switches, in a time-division manner, the quantity of the first light to be applied to the observation object to a constant light quantity or a light quantity controlled on the basis of the luminance of the pixel corresponding to the predetermined wavelength band in the captured image.

5. The observation system according to claim 4, wherein the captured image is associated with a quantity of the first light applied to the observation object at a time of capturing the image.

6. The observation system according to claim 1, wherein in a case where the quantity of the first light that allows the value of the luminance of the pixel to fall within the predetermined range exceeds a threshold, the light source control circuitry controls the quantity of the first light such that the quantity of the first light is equal to the threshold.

7. The observation system according to claim 1, wherein the plurality of light sources is a plurality of laser light sources.

8. The observation system according to claim 7, wherein the plurality of light sources includes a red light source, a green light source, and a blue light source.

9. The observation system according to claim 1, further comprising:
a white light source that emits white light.

10. The observation system according to claim 1, further comprising:
a special light source that emits light of a wavelength band different from any of the wavelength bands of the plurality of light sources.

11. A light source control apparatus comprising:
light source control circuitry configured to control a quantity of first light to be applied to an observation object from an optical system on a basis of a luminance of a pixel corresponding to a predetermined wavelength band in a captured image of the observation object such that a value of the luminance of the pixel falls within a predetermined range, wherein
the first light includes light emitted from some of a plurality of light sources that emit light of different wavelength bands that can be combined to generate white light, and
the optical system combines the light emitted from the plurality of light sources to generate second light which is white light, and irradiates the observation object with the second light.

* * * * *